United States Patent [19]

Shiner et al.

[11] Patent Number: 4,626,213
[45] Date of Patent: Dec. 2, 1986

[54] DENTAL APPLIANCE

[75] Inventors: James R. Shiner, 3415 Lark St., San Diego, Calif. 92103; Wilbur E. Rule, San Diego, Calif.

[73] Assignee: James R. Shiner, San Diego, Calif.

[21] Appl. No.: 752,308

[22] Filed: Jul. 5, 1985

[51] Int. Cl.$^4$ ............................................. A61C 13/22
[52] U.S. Cl. ................................... 433/173; 433/189
[58] Field of Search ................................. 433/189, 173

[56] References Cited

U.S. PATENT DOCUMENTS

| | | | |
|---|---|---|---|
| 4,209,905 | 1/1980 | Gillings | 433/189 |
| 4,302,189 | 11/1981 | Gillings | 433/189 |
| 4,431,419 | 2/1984 | Portnoy | 433/189 |
| 4,488,875 | 12/1984 | Niznick | 433/173 |

Primary Examiner—Robert Peshock
Attorney, Agent, or Firm—Bruno J. Verbeck

[57] ABSTRACT

A denture-retaining unit comprises a ball and socket structure, the socket being adapted for incorporation into a denture. The ball is a sphere having a truncated portion providing a flat base adapted for magnetic engagement with a flat face of a magnetizable keeper, which keeper is adapted to be secured to a support member extending from the jaw. A characterizing feature of the unit is that it permits lateral movement between the denture in which the socket is embedded and the keeper, while the flat faces of the keeper and the sphere remain fully magnetically engaged.

8 Claims, 5 Drawing Figures

DENTAL APPLIANCE

TECHNICAL FIELD

The present invention relates in general to dental appliances, and more particularly to such appliances which employ magnetic retention means.

BACKGROUND ART

The many problems associated with adhering dentures to gum tissue by means of adhesives has resulted in the development of various retention means based on the use of magnets. Examples of dental appliances of the general type to which this invention relates can be found in U.S. Pat. Nos. 4,184,252; 4,209,905; 4,302,189; and our copending patent application Ser. No. 06/671,749, filed 11/15/84. Each of these discloses a relatively new generation magnet, specifically a cobalt-rare earth magnet, mounted in an artificial denture in such a way that a full face of the magnet is exposed substantially at the gum tissue-conforming surface of the denture. A magnetizable element is mounted to a structural support associated with the denture wearers jawbone in such a way that a surface thereof is exposed for abutting engagement with the pole face of the magnet in the denture. In one embodiment of the prior art, the magnet is generally cylindrical in shape and magnetically polarized in such a way that only one pole face thereof engages the exposed surface of the magnetizable element. Other embodiments disclose a generally U-shaped magnetic body comprising a spaced-apart parallel pair of elongated bar magnets joined at their adjacent distal ends remote from the magnetizable element by a ferromagnetic bridge, the magnets being inverted with respect to each other so as to be oppositively magnetically polarized. The device disclosed in our aforesaid copending patent application comprises a denture member having a gum-tissue-conforming surface, and a generally U-shaped magnet member secured to the denture member, and having a spaced-apart pair of pole faces which are aligned in a common plane and exposed adjacent the gum-tissue-conforming surface. The said magnet member includes a magnetic bridge element having a spaced-apart pair of surface portions exhibiting opposite magnetic polarity, and a pair of magnetizable leg elements mounted on opposite sides of the magnetic bridge element in intimate abutting contact with substantially the whole of the magnetically polarized surface portions.

One of the disadvantages of certain prior art devices stems from the fact that because in those devices the magnet face and the keeper face are flat, this poses problems when there is loading on the overdenture at points distant from where the magnet-keeper system is located. When such pressure, or loading, especially in the posterior part of the overdenture occurs, a space or gap is caused to appear between the flat faces of the keeper and magnet, which gap disappears when the pressure or load is terminated and the flat faces come together again, that being accompanied by an unwelcome clicking noise.

Attempts to remedy this and other undesirable factors have been manifested in the development of concave/convex mating faces, rather than flat surfaces, on the magnet face and keeper face, to allow the overdenture to move slightly during chewing while remaining in contact with each other without the faces "gaping". These attempts however, have not been entirely satisfactory. One reason for this is that introduction of a curved surface either into the magnet face or the face of the keeper results in undesirable concentrations of force between the two, whenever lateral force is imposed on either an amputated tooth or an implant post to which the keeper is secured. A curved-surface-to-curved-surface relationship works well only when vertical forces are present. Lateral forces drive the cup shape of one member against the dome shape of the other locking one against the other, and resulting in the transfer of such lateral force to the tooth or implant post.

It is well known in the art that lateral forces imposed on a tooth, or teeth, are responsible for much of the periodontal disease which afflicts mankind. By way of further explanation: the only means by which an orthodontist can reposition teeth require the application of a lateral force or forces to exert pressure on those teeth. During this procedure, the bone which is positioned ahead of the tooth being moved, is destroyed. The tooth then moves into this new void—which has resulted from bone destruction. Thus, if a tooth is constantly being subjected to lateral movement, especially lateral movement in all directions, it is apparent that the bone will be destroyed on all sides, eventually, resulting in the loss of the tooth, root, or implant, which ever is being subjected to these lateral forces.

DISCLOSURE OF THE INVENTION

An important object of the present invention is to provide a magnetic denture retention unit which has incorporated into the structure thereof improved means for effecting the magnetic retention of a denture within a wearers mouth.

A further object is to provide such a magnetic denture retention unit which permits a flat face of a magnet member secured to the denture, to remain in full, face-to-face magnetic contact, during articulation, with the mating flat face of a keeper attached to a tooth piece or implant.

A still further object is to provide means which permits a flat magnetic face in a denture to remain in contact with the flat face of a ferromagnetic keeper secured to a tooth piece, or implant, whenever a cantilevered portion of the denture is subjected to stress by a displacing force, while simultaneously relieving stress on the tooth piece or implant.

The foregoing and other objects of the present invention are accomplished in a dental appliance which comprises a denture member having a gun-tissue-conforming surface, a magnet member secured to the denture member, the magnet member being the ball of a ball-and-socket structure, with the ball portion of the structure being in the form of a sphere which has at least one truncated portion, whereby to provide a flat magnetic face which is adapted to abut with and be in full magnetic contact with, a flat-faced keeper which is secured to a tooth, root, implant, or shank replacing such tooth.

The ball, or sphere, which is actually a truncated ball, or sphere, comprises a magnet forming part of the interior of the ball, and magnetizable leg elements, as shown in the drawings. In brief, the ball and socket structure, a characterizing feature of our invention, permits the flat magnetic face portion of the denture to remain in full contact with the flat face of the tooth piece whenever an unsupported portion of the denture is stressed, especially with a lateral displacing force, without substantial simultaneous lateral stress being applied to the tooth piece.

BRIEF DESCRIPTION OF THE DRAWINGS

The above and other objects of our invention will be best understood by reference to the following description of the invention taken in conjunction with the accompanying drawings, wherein.

BEST MODE FOR CARRYING OUT THE INVENTION

Figure 1:
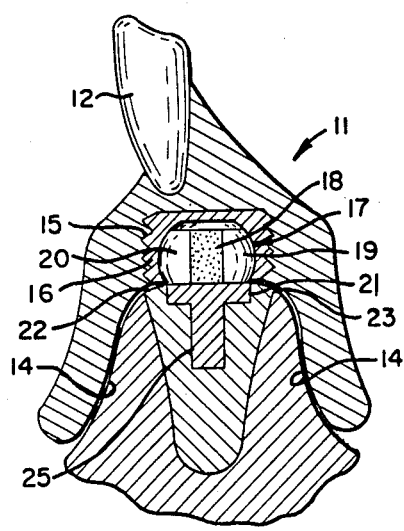
FIG. 1 is a partial cross-sectional view of a preferred embodiment of a dental appliance comprising an overdenture, and incorporating as a part of a magnetic denture retention unit, ball-and-socket therein, in accordance with our invention, when no lateral force is being applied to the overdenture.

Referring now to the drawings, and in particular to FIG. 1, there is shown a preferred embodiment of a magnetic denture retention unit in place, in accordance with our invention, as it appears when no lateral forces are being applied thereto.

For convenience, our magnetic denture-retention unit can be considered as being formed of a first-subunit and a second sub-unit. The first sub-unit is further described as follows: An overdenture 11 having an artificial tooth 12 embedded therein, and having a gum-tissue-conforming surface 13 on the underside thereof is positioned over the natural gums 14 of a denture wearer. A threaded cavity 15 extends inwardly of the overdenture 11 for threadably receiving socket ring 16, the socket ring 16 being dimensioned to receive and support magnetic member 17, comprising a bar magnet 18, and magnetizable leg elements 19, and 20, together forming a modified sphere. Magnetic forces emanating from magnetic member 17 function to retain the denture 11 in place upon the gums 14 as a result of magnetic attachment to a second sub-unit which includes a magnetizable keeper element 21, which is secured to a support member 22. Support member 22 may take various forms as, for example, a dental implant mounted for support by the denture wearer's jawbone. In providing such implant, illustratively, the tooth or teeth are first after suitable treatment, amputated to a level which is above the gum ridge 23, and then drilled to provide a recess for conformably accomodating a shank portion 25 which is integral with keeper element 21, and extends downwardly therefrom.

Figure 3:
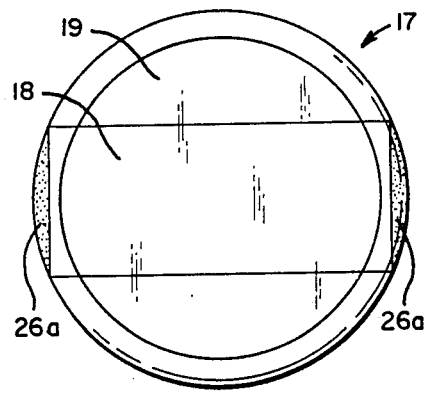
FIG. 3 is a plan view of the magnet assembly shown in FIGS. 1 and 2.

Referring to FIG. 3, the rectangular magnet 18 as shown is 0.170" long and 0.100" wide and 0.080" thick. Epoxy filler 26a is applied to the ends of the magnet 18 and shaped to conform to and be part of the spherical surface of magnet member 17.

Figure 4:
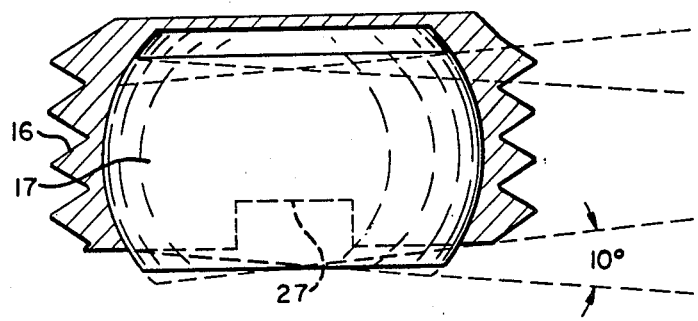
FIG. 4 is a sectional side view illustrating the magnetic retention structure shown in claims 1 and 2.

Preferably the face of magnet member 17 projects slightly outside of socket ring 16 (FIGS. 1 and 2); the face of magnet 18 is preferably coated with a protective layer of epoxy material. As shown, the diameter of the magnet face is 0.160" with the diameter of the ball, at its widest, being 0.187". The leg elements 19 and 21 are of 416 stainless steel, FIG. 4 shows the degree of controlled rotatability of the ball 17, which can be, for example, approximately 10°.

Slots 26 and 27 (FIG. 5) are used for insertion of an appropriate tool therein, for threadably positioning the socket ring 16 into cavity 15.

Figure 5:
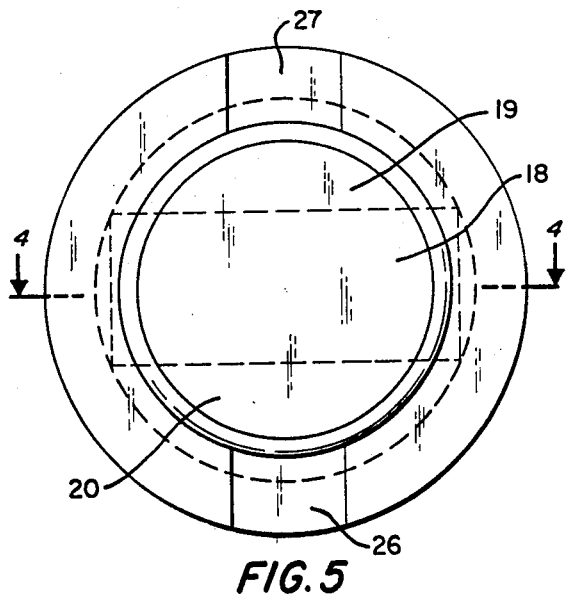
FIG. 5 is a plan view of the socket ring shown in FIGS. 1 and 2.

As illustrated in FIG. 5, the outside diameter of the socket ring 16 is 0.250", the face diameter opening is 0.172", and the ball diameter is 0.187".

Figure 2:
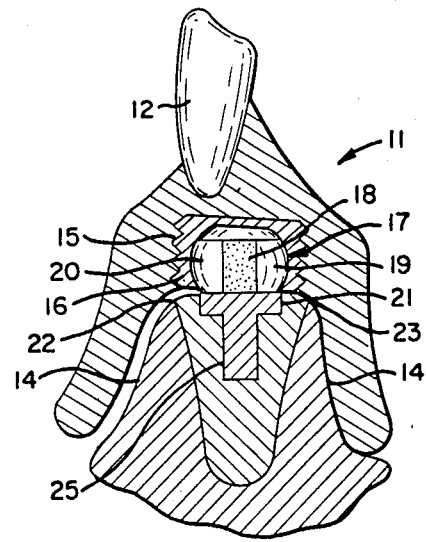
FIG. 2 is a partial cross-sectional view of the same embodiment as shown in FIG. 1, illustrating the functioning of the ball-and-socket structure permitting flat-face-to-flat-face contact of the magnet and the keeper when lateral force is being applied.

As best seen in a comparison of FIGS. 1 and 2, the application of a lateral force on the overdenture 11 permits relative movement of the overdenture 11 with respect to the keeper 21 while maintaining a full magnetic contact between the flat face of the keeper 21 and the corresponding flat face of the magnet member 17, thereby substantially minimizing the destructive action otherwise exerted on the amputated tooth or the implant post which ordinarily occurs when a lateral force is imposed on the denture 11.

While preferred embodiments of the present invention have been illustrated in detail it will be obvious to those skilled in the art that modifications and adaptations of those embodiments, within the skill of the art will be apparent. Accordingly, such adaptations and modifications are to be understood as being within the spirit and scope of the present invention as set forth in the following claims.

We claim:

1. A denture retaining unit comprising a first sub-unit in the form of a ball and socket structure wherein said structure comprises a socket ring which is adapted to receive and house said ball and to be incorporated into a denture, and said ball is in the form of a truncated sphere comprised of a permanent magnet positioned between two segments of said sphere, the poles of said magnet extending at least substantially to opposite surface portions of said sphere, the said segments being of a magnetizable metal, and the flat face-portion of said truncated sphere being adapted for magnetic engagement with a flat face of a magnetizable keeper: and a second sub-unit in the form of a flat-faced magnetizable keeper adapted to be secured to a support member extending from the jaw inside the mouth.

2. The denture retaining unit of claim 1 wherein said magnet comprises cobalt and a rare earth.

3. The denture retaining unit of claim 1 wherein said sphere segments and said keeper comprise ferromagnetic stainless steel.

4. The denture retaining unit of claim 1 wherein that end of said socket ring which is to be placed farthest inside the denture, is sealed, the inner portion of said seal being adapted to permit rotary movement of said ball within said socket.

5. The denture retaining unit of claim 1 wherein the said sphere projects out of said socket sufficiently to permit rotation of the sphere without separation of the face-to-face engagement of the flat portions of said sphere and said keeper, during lateral relative movement between said sub-units.

6. The denture retaining unit of claim 1 wherein the ends of said magnet are covered with a protective coating, the coating conforming in curvature of the sphere without projecting beyond the surface of said sphere.

7. The denture retaining unit of claim 1 wherein said ring is threaded for attachments to a denture.

8. The denture retaining unit of claim 1 wherein the said sphere is also truncated across the portion of the sphere which is opposite the truncated portion which is adapted for magnetic contact with the said keeper, whereby to limit the degree of movement of the sphere within the socket.

* * * * *